United States Patent
Zhang et al.

(10) Patent No.: US 11,395,823 B2
(45) Date of Patent: Jul. 26, 2022

(54) TOPICAL ADMINISTRATION OF MEK INHIBITING AGENTS FOR THE TREATMENT OF SKIN DISORDERS

(71) Applicant: Duke University, Durham, NC (US)

(72) Inventors: Jennifer Yunyan Zhang, Durham, NC (US); Adela Rambi G. Cardones, Durham, NC (US); Yingai Jin, Durham, NC (US); Simone Degan, Durham, NC (US); Russell Hall, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 16/960,466

(22) PCT Filed: Jan. 9, 2019

(86) PCT No.: PCT/US2019/012878
§ 371 (c)(1),
(2) Date: Jul. 7, 2020

(87) PCT Pub. No.: WO2019/139970
PCT Pub. Date: Jul. 18, 2019

(65) Prior Publication Data
US 2021/0060018 A1    Mar. 4, 2021

Related U.S. Application Data

(60) Provisional application No. 62/615,220, filed on Jan. 9, 2018.

(51) Int. Cl.
*A61K 31/519* (2006.01)
*A61P 17/06* (2006.01)
*A61P 17/16* (2006.01)
*A61P 35/00* (2006.01)
*A61K 9/00* (2006.01)

(52) U.S. Cl.
CPC .......... *A61K 31/519* (2013.01); *A61K 9/0014* (2013.01); *A61P 17/06* (2018.01); *A61P 17/16* (2018.01); *A61P 35/00* (2018.01)

(58) Field of Classification Search
CPC .... A61K 31/519; A61K 9/0014; A61K 45/06; A61P 17/06; A61P 17/16; A61P 35/00
USPC ........................................................ 514/264
See application file for complete search history.

(56) References Cited

U.S. PATENT DOCUMENTS

| | | |
|---|---|---|
| 2013/0273061 A1 | 10/2013 | Huang et al. |
| 2014/0093568 A1 | 4/2014 | Bray et al. |

(Continued)

OTHER PUBLICATIONS

International Search Report and Written Opinion, International Patent Application No. PCT/US2019/012878, dated Mar. 29, 2019, 11 pages.

*Primary Examiner* — Taylor V Oh
(74) *Attorney, Agent, or Firm* — Casimir Jones, SC; Robert A. Goetz

(57) ABSTRACT

The instant disclosure provides methods and compositions related to discovery that topical administration of MEK inhibitors for the treatment of skin disorders (e.g., skin cancer, inflammatory skin disorders) is accomplished with markedly reduced dosage levels in comparison with oral administration dosage levels. Therapeutic and/or prophylactic uses and compositions of known MEK inhibitors are described.

18 Claims, 7 Drawing Sheets

(56) References Cited

U.S. PATENT DOCUMENTS

| | | |
|---|---|---|
| 2014/0128442 A1* | 5/2014 | Krell .................. A61P 43/00 |
| | | 514/394 |
| 2015/0023915 A1 | 1/2015 | Morrison et al. |
| 2015/0111869 A1 | 4/2015 | Belvin et al. |
| 2015/0126533 A1 | 5/2015 | Arita et al. |
| 2015/0231109 A1 | 8/2015 | Rodriguez-lopez |
| 2016/0367539 A1 | 12/2016 | Saha et al. |

* cited by examiner

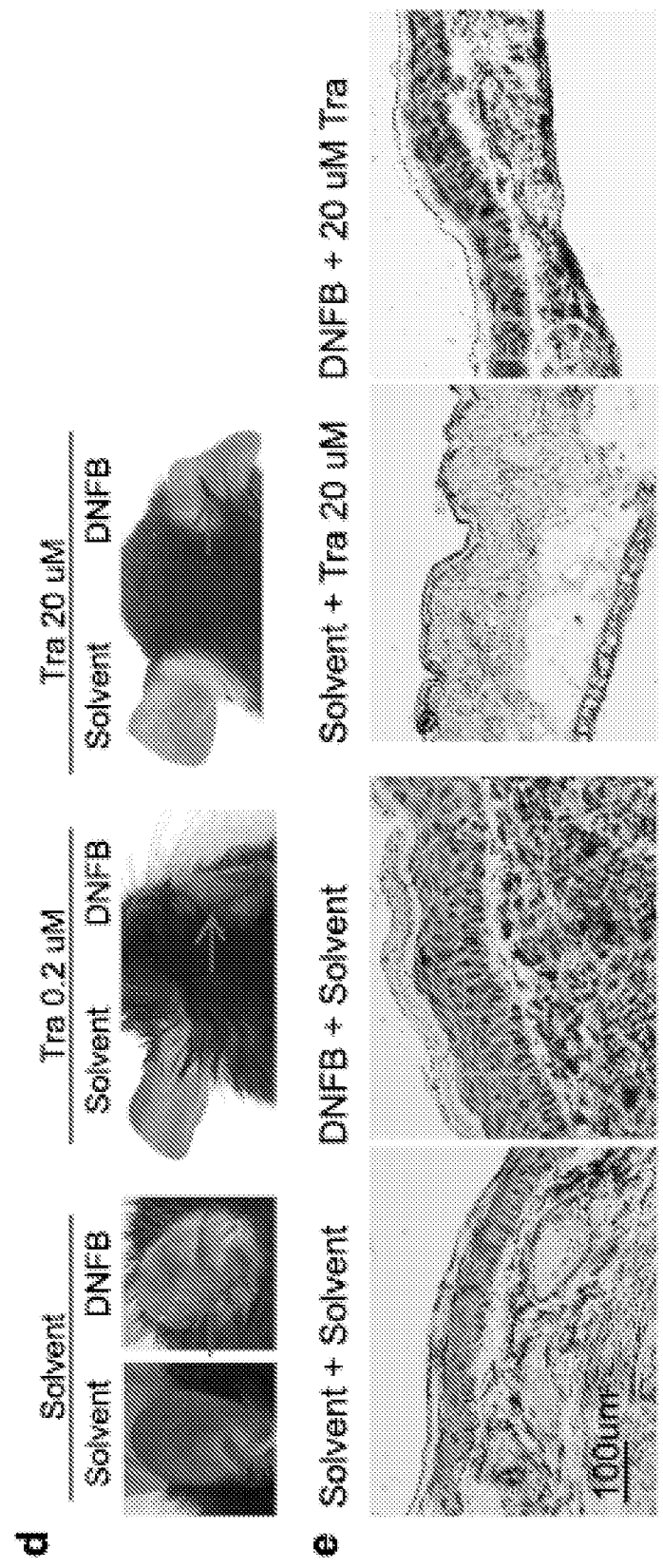

a. Human psoriatic skin lesions.

b. Human cutaneous GVHD lesional tissues

TOPICAL ADMINISTRATION OF MEK INHIBITING AGENTS FOR THE TREATMENT OF SKIN DISORDERS

CROSS REFERENCE TO RELATED APPLICATIONS

This applications is a national phase application under 35 U.S.C. § 371 of PCT International Application No. PCT/US2019/012878, filed Jan. 9, 2019, which claims priority to and the benefit of U.S. Provisional Application No. 62/615,220, filed Jan. 9, 2018, which are hereby incorporated by reference in their entireties.

FIELD OF THE INVENTION

The instant disclosure provides methods and compositions related to discovery that topical administration of MEK inhibitors for the treatment of skin disorders (e.g., skin cancer, inflammatory skin disorders) is accomplished with markedly reduced dosage levels in comparison with oral administration dosage levels. Therapeutic and/or prophylactic uses and compositions of known MEK inhibitors are described.

BACKGROUND OF THE INVENTION

The skin is the outer most barrier of the body and keratinocytes form the primary barrier cells of the skin. Dysregulation of cell signaling pathways such as the MEK/ERK signaling pathway in keratinocytes underscores a wide range of skin disorders, including skin cancer and many common inflammatory skin diseases (e.g., atopic dermatitis, psoriasis, and cutaneous graft versus host disease). A fix-all cure for many of the common skin disorders is not available. Most of the current treatments, including topical steroids as well as systemic non-biologic and biologic drugs, target immune cells. Responses to these therapies are often complicated by an increased risk of infection, organ damage, and the development of resistance to a previously effective treatment.

As such, improved treatment options are needed. The present invention addresses this need.

SUMMARY

The BRAF/MEK/ERK signaling pathway plays a pivotal role in cancer and a wide array of inflammatory skin lesions including psoriasis and atopic dermatitis. This pathway has been successfully targeted with a number of small molecular compounds. Among these is the MEK inhibitor trametinib which was FDA-approved for melanoma in 2013 and is currently in clinical use for several other cancers. Oral dose trametinib effectively regresses melanoma and prevents secondary skin cancers otherwise induced by BRAF inhibitors. However, like many other oncokinase inhibitors, oral trametinib is associated with substantial side effects, discouraging its use for non-malignant diseases. As such, alternate manners of administering MEK inhibitors which could take advantage of the therapeutic effects while avoiding the substantial side effects would be quite beneficial.

Experiments conducted during the course of developing embodiments for the present invention investigated the topical application of MEK inhibitors in the treatment of skin cancer and inflammatory skin disorders. Specifically, such experiments assessed the in vivo effects of a topical application of a MEK inhibitor (e.g., trametinib) on four different animal skin disease models, including the oncogenic Braf-driven skin cancer and inflammation model, the 2,4-dinitrofluorobenzene (DNFB)-induced atopic dermatitis, UV-induced skin carcinogenesis, and the imiquimod (IMQ)-induced psoriasis model. It was determined that 1) keratinocyte targeted oncogenic Braf mutation results in postnatal lethality with inflammatory skin defects; 2) epidermis-targeted Braf mutation in adults induces epidermal and sweat gland neoplasia; 3) topical application of a MEK inhibitor (trametinib) effectively treats skin and oral lesions of Braf mutant mice; 4) topical application of a MEK inhibitor (trametinib) reducesDNFB-induced skin inflammation; 5) topical application of a MEK inhibitor (trametinib) reduces UV-induced skin carcinogenesis; and 6) MEK is activated in human psoriasis and GVHD skin and oral lesions, and 7) topical application of a MEK inhibitor (trametinib) reduces IMQ-induced epidermal thickening. Such results indicate that topical application of a MEK inhibitor (e.g., trametinib) effectively inhibits mutant Braf and UV-induced epidermal neoplasia and inflammation, and reduces DNFB-induced dermatitis. Moreover, such results indicate that the effective topical dose of the MEK inhibitor for prevention of skin inflammation is less than 0.1% of the oral dose used for cancer therapy. Such a lower dosage of the MEK inhibitor permitted through topical application, in comparison with systemic application dosages, represents a non-toxic dosage, which is demonstrated by the overall animal appearance and the normal histological appearance of kidney, spleen, and liver tissues.

Accordingly, the instant disclosure is based, at least in part, upon the discovery that topical administration of MEK inhibitors for the treatment of skin disorders (e.g., skin cancer, inflammatory skin disorders) requires markedly reduced dosage levels in comparison with oral administration dosage levels. Such discovery has thereby inspired a new strategy for treatment or prevention of such skin disorders in a subject—specifically, one based upon topical administration of a MEK inhibitor to the subject. Topical application of MEK inhibitors (e.g., trametinib, cobimetinib, binimetinib, selumetinib, and tetrathiomolybtate) for treatment or prevention of skin disorders (e.g., skin cancer, inflammatory skin disorders) and/or an associated disease or disorder is specifically contemplated.

In certain embodiments, the present invention provides methods of treating or preventing a skin disorder in a patient in need thereof, the method comprising topical administration of a pharmaceutical composition to the area in need of treatment, wherein the pharmaceutical composition comprises a therapeutically effective amount of a MEK inhibiting agent and a pharmaceutically acceptable diluent or carrier, wherein the pharmaceutical composition is in a form selected from ointments, gels, creams, lotions, oil-in-water emulsions, water-in-oil emulsions, microemulsions, foams, sprays, mousses, patches, powders, pastes, and medicated plasters.

In some embodiments, the topical administration of a pharmaceutical composition to the area in need of treatment results in percutaneous absorption of the therapeutically effective amount of the MEK inhibiting agent into the skin.

In some embodiments, the topical administration of a pharmaceutical composition to the area in need of treatment comprises topically applying the pharmaceutical composition (e.g., rubbing the composition onto/into the area in need of treatment) in an amount sufficient to cover the area in need of treatment in such a manner or amount as to provide the desired therapeutic effect. In some embodiments, such administration comprises topically applying the pharmaceutical composition (e.g., rubbing the composition onto/into the area in need of treatment) in an amount sufficient to cover the area in need of treatment plus a margin of healthy skin or tissue surrounding the affected area, for example, a margin of about 0.5 inches in such a manner or amount as to provide the desired therapeutic effect.

Such methods are not limited to particular amount of the MEK inhibiting agent within the pharmaceutical composition. In some embodiments, the wherein the MEK inhibiting agent is present at from about 0.01% to about 10% (w/w). In some embodiments, the MEK inhibiting agent is present at from about 0.3% to about 3%. In some embodiments, the MEK inhibiting agent is present at about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10% (w/w).

Such methods are not limited to a specific type or kind of pharmaceutically acceptable diluent or carrier. In some embodiments, the pharmaceutically acceptable diluent or carrier comprises at least one substance selected from the group comprising water; alcohols selected from monohydric alcohols having from 1 to 18 carbons, such as methanol, ethanol, propanol, isopropanol, butanol, hexanol, cetyl alcohol, stearyl alcohol, and the like; dihydric and polyhydric alcohols, such as propylene glycol, glycerol; hexanetriols, such as 1,2,6-hexanetriol, sorbitol, 1,3-butanediol, 2,3-butanediol; lower alkyl ethers of glycols having from 1 to 6 carbons such as the monomethyl or monoethyl ether of ethylene or diethylene or propylene or dipropylene glycol, propylene glycol or dipropylene glycol monomethyl ethers, diethylene glycol monoethyl ether, ethylene glycol monomethyl ether; polyethylene glycols having molecular weights of from 100 to 8,000, preferably in the range 4,000; esters of aliphatic monobasic and dibasic acids having from 2 to 22 carbons and monohydric alcohols having from 1 to 20 carbons, di- and polyhydric alcohols having from 2 to 20 carbons, and sugar alcohols such as isopropyl myristate, isopropyl palmitate, myristyl myristate, cetyl stearate, methyl stearate, isopropyl sebacate, methyl sebacate, sucrose monolaurate, sucrose monostearate, and the like; mannitol, xylitol, sorbitol and monohydric alcohols having from 1 to 6 carbons, such as methanol, ethanol, propanol, isopropanol, butanol, or hexanol.

In some embodiments, the pharmaceutical composition also comprises additional therapeutic agents for treating the skin disorder.

In some embodiments, the pharmaceutical composition further comprises an emulsifier.

In some embodiments, the pharmaceutical composition further comprises a viscosity-increasing agent.

In some embodiments, the pharmaceutical composition further comprises a penetration enhancer. In some embodiments, the penetration enhancer is selected from the group comprising DMSO, 2-(2-Ethoxyethoxy)ethanol, dimethyl isosorbide, C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C8 diacids such as diisopropyl adipate; monoglycerides of C8-C22 fatty acids such as glyceryl monolaurate; tetrahydrofurfuryl alcohol polyethylene glycol ether; polyethylene glycol; propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; terpenes; macrocyclic enhancers such as macrocyclic ketones, for example, 3-methylcyclopentadecanone, 9-cycloheptadecen-1-one, cyclohexadecanone, and cyclopentadecanone; macrocyclic esters such as pentadecalactone.

Such methods are not limited to treating a particular type or kind of skin disorder. In some embodiments, the skin disorder is any skin disorder characterized by a Braf mutation. In some embodiments, the skin disorder is a skin cancer. In some embodiments, the skin cancer is selected from squamous cell carcinoma (SCC), basal cell carcinoma (BCC), hyperkeratosis, actinic keratosis, sebaceous adenoma, UV induced skin cancer, and syringoma. In some embodiments, the skin disorder is an inflammatory skin condition. In some embodiments, the skin disorder is selected from atopic dermatitis, GVHD, psoriasis, and pruritis.

Such methods are not limited to a particular MEK inhibiting agent. In some embodiments, the MEK inhibiting agent is selected from trametinib (N-(3-{3-Cyclopropyl-5-[(2-fluoro-4-iodophenyl)amino]-6,8-dimethyl-2,4,7-trioxo-3,4, 6,7-tetrahydropyrido[4,3-d]pyrimidin-1 (2H)-yl}phenyl)acetamide), pyrrole derivatives, TAK-733 (one of a series of 8-methylpyrido[2,3-d]pyrimidine-4,7(3H,8H)-dione derivatives), CH4987655 and RDEA119/BAY 869766, cobimetinib ((S)-[3,4-Difluoro-2-(2-fluoro-4-iodophenylamino) phenyl][3-hydroxy-3-(piperidin-2-yl)azetidin-1-yl] methanone), binimetinib (5-((4-bromo-2-fluorophenyl) amino)-4-fluoro-N-(2-hydroxyethoxy)-1-methyl-1H-benzo [d]imidazole-6-carboxamide), selumetinib (6-(4-bromo-2-chloroanilino)-7-fluoro-N-(2-hydroxyelhoxy)-3-methylbenzimidazole-5-carboxamide), PD-325901, CI-1040, PD035901, tetrathiomolybtate, and TAK-933.

In some embodiments, the skin disorder is a skin cancer, and the MEK inhibiting agent is trametinib, wherein the dosage amount of the trametinib is approximately 0.2 mg.

In some embodiments, the skin disorder is a skin cancer, and the dosage of the MEK inhibiting agent is approximately 10× less than a therapeutically effective oral dosage for trametinib in the treatment of melanoma or the same type of skin cancer.

In some embodiments, the disorder is a Braf-induced tumor, and the concentration of the MEK inhibiting agent within the composition is approximately 1.5 mM.

In some embodiments, the composition is used to prevent UV-induced skin cancer, and the concentration of the MEK inhibiting agent within the composition is approximately between 10 µM and 30 µM.

In some embodiments, the disorder is an inflammatory skin disorder, and the concentration of the MEK inhibiting agent within the composition is approximately between 0.2 mM and 60 mM.

In some embodiments, the skin disorder is an inflammatory skin condition, and the dosage of the MEK inhibiting agent is approximately 10,000× less than a therapeutically effective oral dosage for the same MEK inhibiting agent for treating the same inflammatory skin condition.

In certain embodiments, the present invention provides kits comprising, for example, a pharmaceutical composition as recited in claim 1 and instructions for topically administering the pharmaceutical composition to a patient having a skin disorder.

Figure 2:
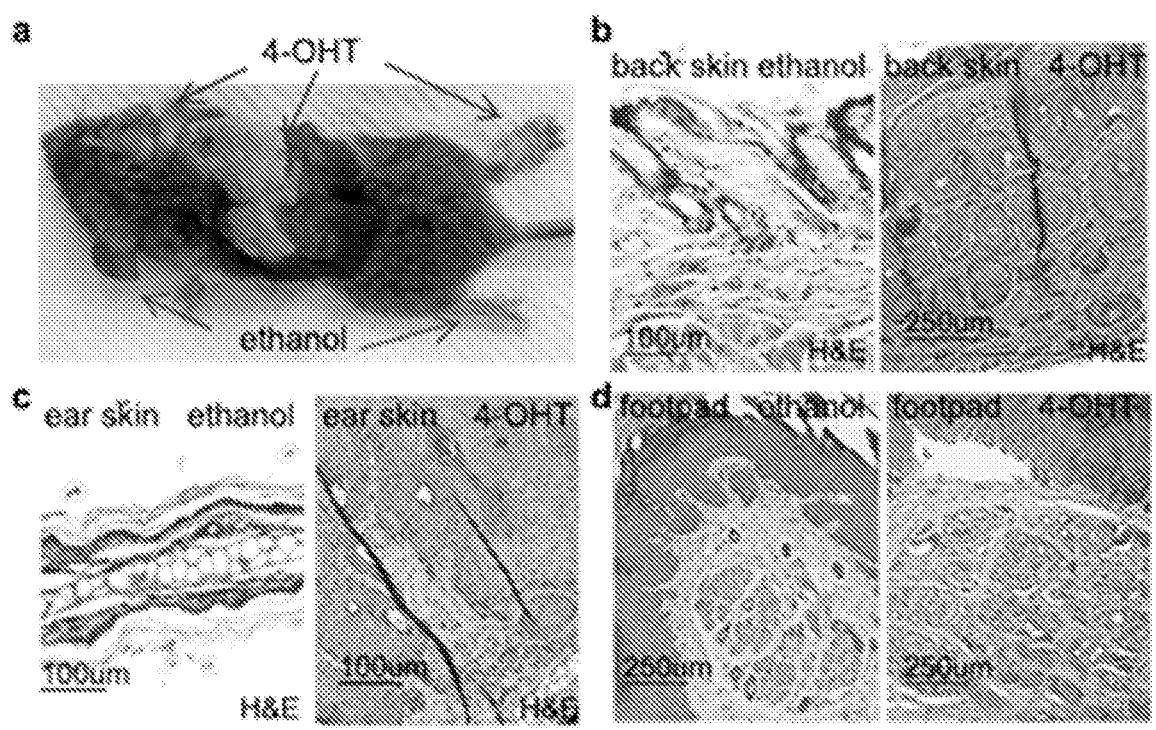

FIG. 2: Braf mutation in adult skin induces epidermal and sweat gland neoplasia. (a) Clinical image of a K5-CreER.Braf$^{CA/+}$ mouse 2 weeks after topical treatment with ethanol and 4-OHT. (b-d) H&E staining of (b) back skins, (c) ear skins, and (d) footpads treated with ethanol or 4-OHT.

Figure 3:
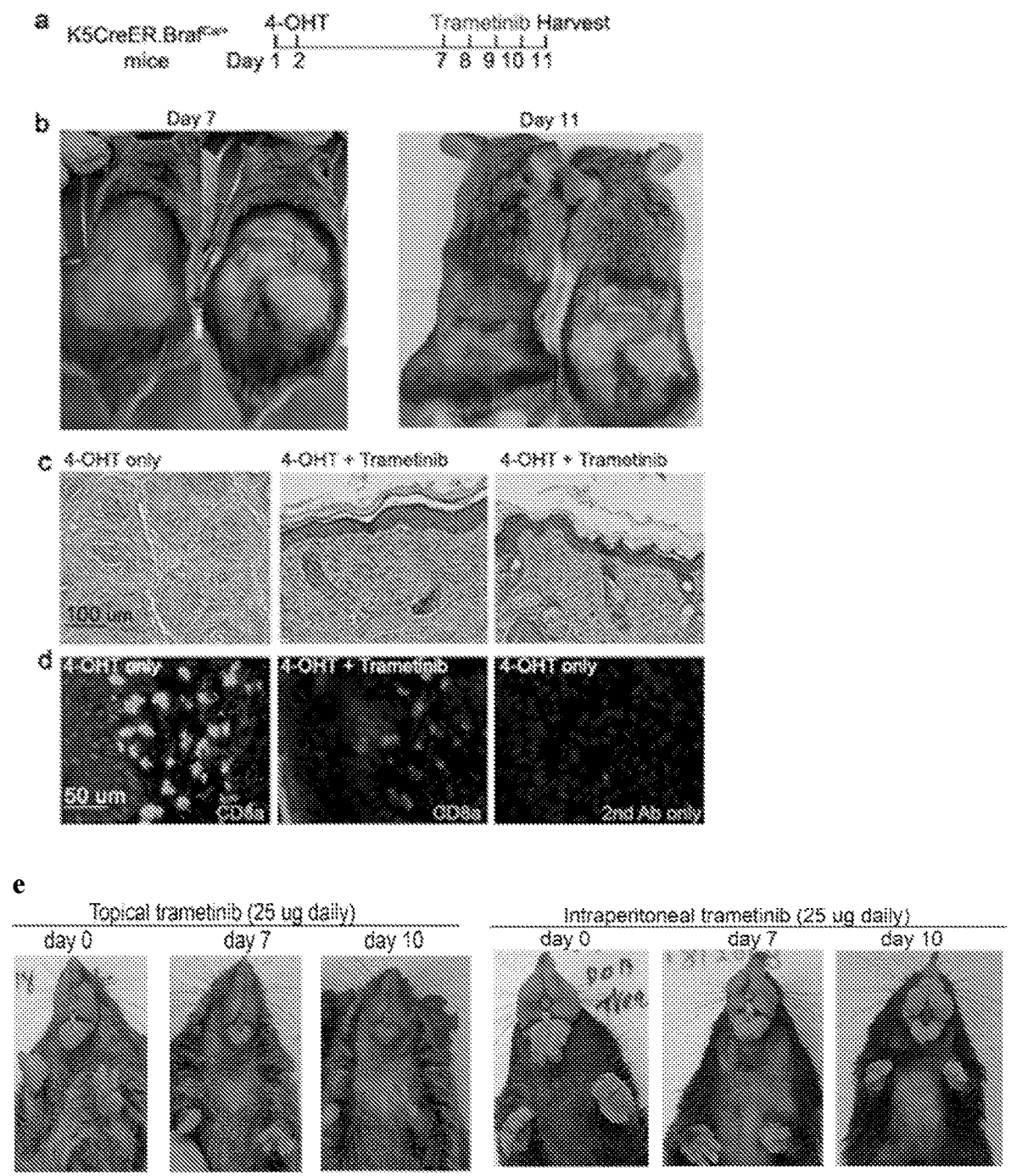

FIG. 3: Topical trametinib regresses skin tumor growth and inflammation induced by Braf mutation. (a) Topical treatment scheme of K5CreER.Braf$^{ca/+}$ mice skin with 4-OHT and trametinib. (b) Clinical images of mice before and after treatment with trametinib. (c) H&E staining. (d) Immunostaining for CD8 [gray-scaled green]. Nuclei [gray-scaled blue].

Figure 4:
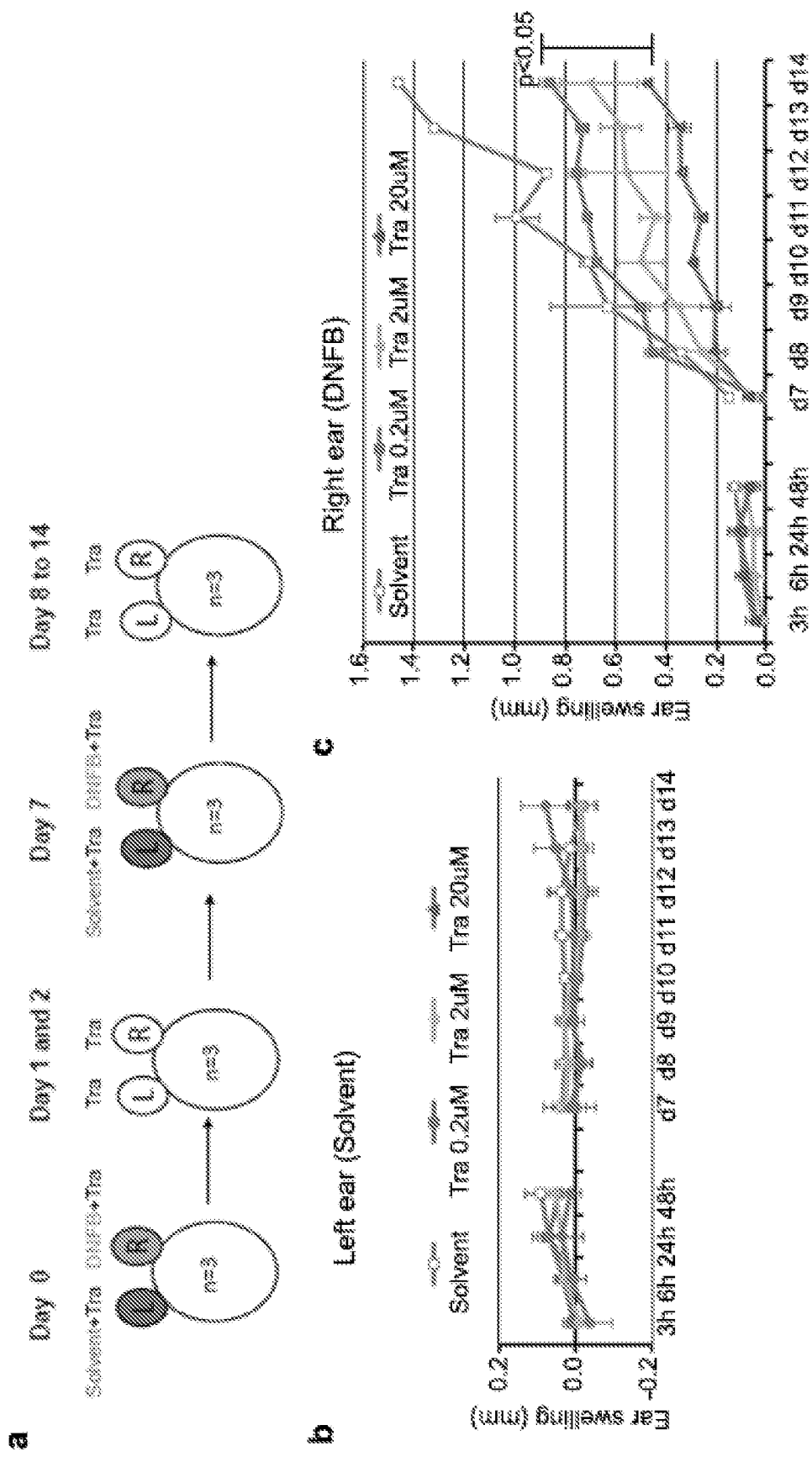

FIG. 4: Topical trametinib inhibits DNFB-induced skin inflammation. (a) Treatment scheme of mouse ear lobes (n=3/group). (b-c) Swelling of the (a) left and (b) right ears. Ear swelling was obtained via deduction of the beginning thickness from that of the same ear measured at later time-points. Line graphs represent time-course average ear swelling of each group+SD. P-values of less than <0.05 were obtained via two-tiered student T-Test comparing data of 2 and 20 µM doses to that of control or 0.2 µM dose. (d) Clinical images of ears treated with solvent and DNFB along with 0, 0.2 and 20 µM trametinib. (e) H&E staining.

Figure 5:
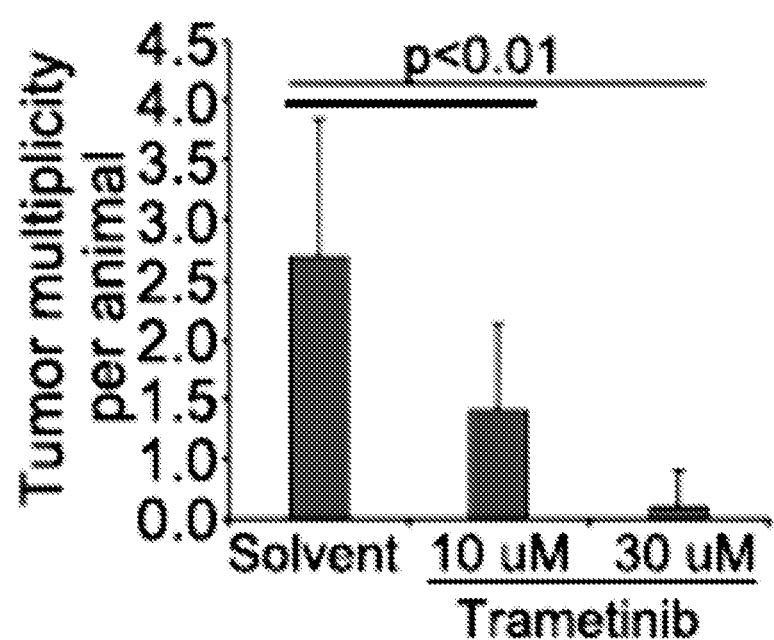

FIG. 5: Topical trametinib inhibits UV-induced skin carcinogenesis. Graph represents average number of tumors in mice (n=10/group). Animals were treated three times per week with broadband UVB (160-180 mJ) along with topical treatment of solvent, 10 µM and 30 µM trametinib.

Figure 6:
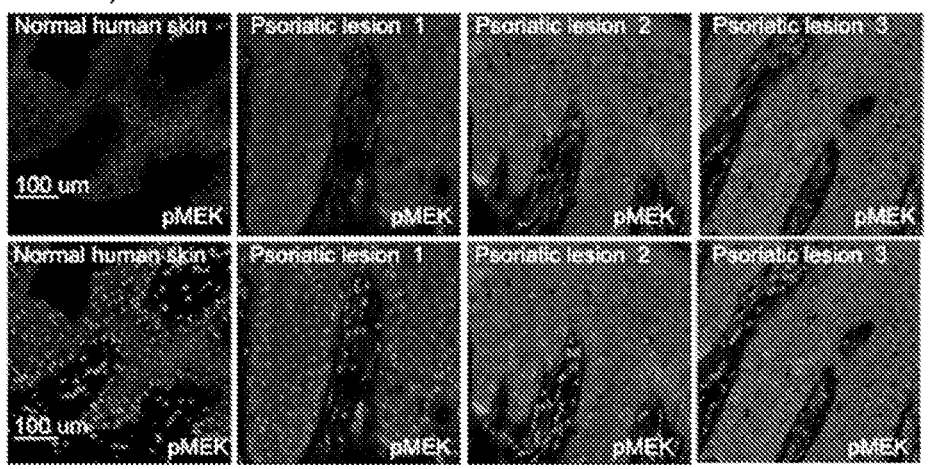
Figure 6:
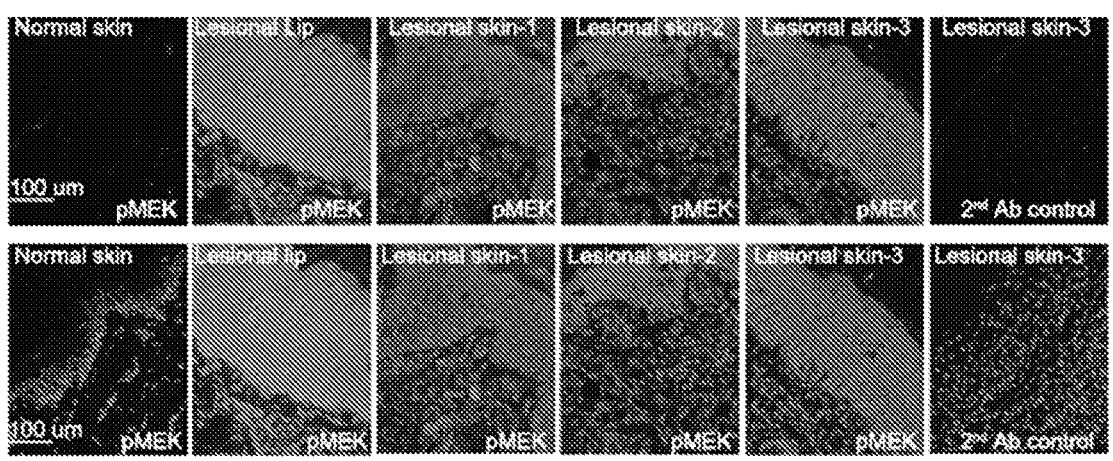

FIG. 6: MEK activation is increased in human psoriatic and cutaneous GVHD lesional skins. (a-b) Immunofluorescent staining for pMEK of (a) human psoriatic lesional skin samples and (b) cutaneous and oral GVHD lesions along with normal human skin sections. pMEK [gray-scaled orange]. Nuclei [gray-scaled blue]. Representative images were shown.

DETAILED DESCRIPTION

MAPK represents a family of serine/threonine protein kinases that are widely expressed in eukaryotic cells. Previous studies found four different MAPK subfamilies: i) ERK (ERK1/ERK2); ii) c-Jun N-terminal kinase (JNK); iii) ERK5; and iv) p38 MAPK (p38) (see, Iyoda K, et al., Cancer Am Cancer Soc. 2003; 97:3017-3026). These MAPKs can be activated by various stimuli, such as UV and growth factors, as well as inflammatory cytokines. After activation, the MAPK signaling pathways regulate cellular proliferation, differentiation and apoptosis (see, Huynh H, et al., BMC Gastroenterol. 2003; 3:19) (see, Chung E, et al., Immunol Res. 2011; 49:248-268).

The Ras/Raf/MEK/ERK cascade represents one of the most commonly overactivated oncogenic signaling pathways in cancer and inflammatory disorders. Various mechanisms can activate the Ras/Raf/MEK/ERK cascade in tumor cells: i) genetic mutation of Ras and Raf proteins, ii) chromosome ectopic, such as BCR-ABL; iii) cytokine mutations, such as Flt-3, Fms and Kit; and iv) overexpression of wild or mutant receptors, such as epidermal growth factor receptor (EGFR). The Ras/Raf/MEK/ERK cascade reaction activates transcription factors and regulates gene expression. Briefly, the process involves: i) Ras recruits and activates the protein kinase Raf; ii) Raf serine/threonine protein kinase promotes MEK1/2 (MAPK/ERK kinase) dual-specificity protein kinase and the activation of ERK1/2; and iii) activated ERK1/2 phosphorylates downstream substrates including transcription factors, leading to altered gene expression (see, Zhang Z, et al., BMC Med. 2009; 7:41) and regulation of cell cycle, apoptosis, differentiation, and migration, as well as cellular metabolism (see, Steelman L S, et al., Leukemia. 2004; 18:189-218).

The RAS/RAF/MEK/ERK signaling pathway plays a central role in a wide array of skin cancers, including melanoma, squamous cell carcinoma (SCC), basal cell carcinoma (BCC), hyperkeratosis, actinic keratosis, sebaceous adenoma, and syringoma. In addition, this pathway is involved in inflammatory skin diseases, including psoriasis, allergic and atopic dermatitis, scleroderma, cutaneous graft-vs-host disease. Moreover, BRAF/MEK/ERK signaling acts in both epidermal and neuronal cells to promote itch or pruritus, an unpleasant sensation associated with a wide range of skin abnormalities.

The BRAF and MEK oncokinases have been successfully targeted for cancer therapy with a number of small molecular compounds. Indeed, Ras/Raf/MEK/ERK signal transduction pathways are important targets in cancer treatment research. Inhibitors of Ras, Raf, MEK, ERK and other downstream molecules have been developed and partially used in clinical trials (see, Friday B B, et al., Clin Cancer Res. 2008; 4:342-346).

Skin cancer is by far the most common cancer of human body, accounting for more cases than the combined incidences of breast, prostate, lung and colon cancers. In the US alone, BCC and SCC have an annual incidence of approximately 4 and 1 million new cases, respectively. While a majority of skin cancers can be treated by surgical excision, surgery can lead to significant scarring and morbidity. Non-surgical treatment strategies are eminently needed to reduce the heath-care burden and for patients whose cancer is not operable due to the widespread and recurrent growth on the facial and scalp region. The MEK/ERK signaling axis is a well-established onco-driver of SCC. SCC and sryngoma-metaplasia are observed in melanoma patients treated with the Braf$^{V600E}$ inhibitor vemurafenib, an agent that paradoxically activates MEK via interaction with the wild type Braf and c-Raf. These secondary cancers are successfully treated with oral dose trametinib. Additionally, MEK signaling is responsible for the resistance of BCC to the SHH pathway inhibitors, underscoring the potential of targeting MEK as an adjuvant therapy for BCC.

Atopic dermatitis (AD) is a chronic inflammatory skin disease that affects 15-20% of the population in developed country. It is characterized by recurrent eczema accompanied by a chronic intractable itch that leads to an impaired quality of life. About 60% of AD cases start within months after birth and many persist in adults, causing a substantial psychosocial burden on patients and financial burden on the health care system. AD is associated with increased risks of other immunological diseases, such as food allergy, asthma, and allergic rhinitis, as well as mental health disorders. Recent genetic studies have identified loss-of-function of epidermal barrier protein filaggrin and other stratum corneum and tight junctional proteins as a major predisposing factor for AD. BRAF/MEK overactivation in keratinocytes suppresses expression of filaggrin and other barrier proteins, and contributes to the inflammatory responses. Mild forms of AD can be controlled with topical anti-inflammatory therapies, but moderate-to-severe forms often require a combination of systemic treatments consisting of antipruritic and immunosuppressive drugs, phototherapy, and topical compounds.

Psoriasis affects about 125 million patients world-wide with plaque psoriasis accounting for about 90% of the cases. The etiology of psoriasis is very complex and heterogeneous involving immune cells and keratinocytes. A cure is not available and thus the management of this disease is a life-long process, posing a significant challenge to the US and global health care. Current treatments consist of phototherapy (narrow band UVB and PUVA), topical therapy (e.g. Anthralin, salicylic acid, coal tar, corticosteroids and vitamin A, D analogues), non-biological systemic therapy (methotrexate, cyclosporine, acitretin, and apremilast), and biological systemic therapy. The biological therapies, including humanized antibodies antagonistic of TNFα/TNFR1 (adalimumab, etanercept, and infliximab), IL-17A (ixekizumab, secukinumab, and broadlumab), and IL-12/23 (ustekinumab, brodalumab, and ixekizuma), as well as the CD4-T cell binding protein (alfacept), have recently revolutionized the treatment options for many patients. Nevertheless, these new and old therapies primarily target the immune system and are associated with increased risks of end-organ damage, serious infection, skin cancer, development of resistance, and consequently the necessity of switching treatments over-time. The biological therapies are also complicated by the high cost and the requirement of hospital-based drug administration. If uncontrolled, psoriasis carries an increased risk for mortality and comorbidities such as psoriatic arthritis, cardiovascular disease, diabetes, and psychological issues. It is clear that, despite recent advances, there remains a critical need for low cost home-based treatments.

Keratinocytes of psoriatic skin lesions exhibit hyperproliferation and abnormal differentiation, express increased levels of inflammatory molecules, and crosstalk with immune cells to form a feed-forward self-amplifying inflammatory response. Recently, it has become clear that dysregulation of keratinocyte signaling can both trigger and exacerbate skin inflammation. Specifically, the MEK/ERK pathways is highly activated in keratinocytes of human psoriatic skin lesions. Experimental MEK activation in superbasal mouse keratinocytes via transgenic expression of Ras induces hyperproliferative and inflammatory skin lesions resembling human psoriasis. In agreement with the animal data, pustular psoriasis eruption is observed in melanoma patients treated with dabrafenib, a mutant BRAF inhibitor that paradoxically activates MEK via interaction with WT Raf proteins. These findings demonstrate that uncontrolled MEK activation in keratinocytes promotes the progression of psoriasis, underscoring MEK-inhibition as a potential new therapeutic for psoriasis, specifically plaque psoriasis which is characterized by local skin thickening with red plaques and dry scales.

Graft-verse-host disease (GVHD) is a life-threatening complication that occurs in nearly 50% of patients after an allogeneic hematopoietic stem cell transplantation. The skin is the most commonly affected organ in both the acute and chronic forms of this disease. In particular, lichenoid plaques (LP) and sclerosis on the skin and oral mucosa are associated with poor prognosis. Similar to its de novo equivalent (lichen planus), GVHD LP is associated with a high risk of squamous cell carcinoma (SCC). Treatment options for cutaneous GVHD are limited, and the current standard therapy is high dose systemic corticosteroids, which is in itself associated with significant morbidity and mortality. There is therefore a great need for effective and less toxic treatment strategies for this devastating disease. While the exact cause of GVHD is unclear, it unequivocally involves complex interactions between the recipient cells and donor cells. Studies reported so far are primarily focused on investigating the role of immune cells. Little is known about the role of host cells, specifically skin cells whose involvement is a key diagnostic and prognostic feature of chronic GVHD. Recently, it has been demonstrated that the MEK/ERK signaling pathway is critical for alloreactive T-cell expansion in a mouse GVHD model. Oral administration of the MEK-inhibitor trametinib suppresses recipient mouse T-cell alloreactivity without affecting graft-vs-tumor effects. These findings established the preclinical benefit, but also revealed serious side-effects associated with systemic delivery of MEK inhibition.

Experiments conducted during the course of developing embodiments for the present invention investigated the topical application of MEK inhibitors in the treatment of skin cancer and inflammatory skin disorders. Specifically, such experiments assessed the in vivo effects of a topical application of a MEK inhibitor (e.g., trametinib) on four different animal skin disease models, including the oncogenic Braf-driven skin cancer and inflammation model, the 2,4-dinitrofluorobenzene (DNFB)-induced atopic dermatitis, UV-induced skin carcinogenesis, and the imiquimod (IMQ)-induced psoriasis model. It was determined that 1) keratinocyte targeted oncogenic Braf mutation results in postnatal lethality with inflammatory skin defects; 2) epidermis-targeted Braf mutation in adults induces epidermal and sweat gland neoplasia; 3) topical application of a MEK inhibitor (trametinib) effectively treats skin and oral lesions of Braf mutant mice; 4) topical application of a MEK inhibitor (trametinib) reduces DNFB-induced skin inflammation; 5) topical application of a MEK inhibitor (trametinib) reduces UV-induced skin carcinogenesis; and 6) MEK is activated in human psoriasis and GVHD skin and oral lesions, and 7) topical application of a MEK inhibitor (trametinib) reduces IMQ-induced epidermal thickening. Such results indicate that topical application of a MEK inhibitor (e.g., trametinib) effectively inhibits mutant Braf and UV-induced epidermal neoplasia and inflammation, and reduces DNFB-induced dermatitis. Moreover, such results indicate that the effective topical dose of the MEK inhibitor for prevention of skin inflammation is less than 0.1% of the oral dose used for cancer therapy. Such a lower dosage of the MEK inhibitor permitted through topical application, in comparison with systemic application dosages, represents a non-toxic dosage, which is demonstrated by the overall animal appearance and the normal histological appearance of kidney, spleen, and liver tissues.

Topical application of a MEK inhibitor reaps the benefits of MEK-inhibition and avoids systemic toxicity. This idea is supported by multiple lines of evidence demonstrating the importance of MEK function in various cutaneous and oral aberrations. First, MEK/ERK is required for collagen I induction by PDGFR-autoantibodies that are commonly detected in sclerotic GVHD patients. Consistently, MEK/ERK signaling is essential for fibroblast-mediated matrix contraction. Second, melanoma patients treated with vemurafenib, a Braf$^{V600E}$-inhibitor that paradoxically activates MEK via interaction with the wild type Braf and c-Raf, are prone to the development of GVHD relevant epidermal aberrations, including hyperkeratosis, sryngomametaplasia, and SCC. These lesions are successfully treated with oral doses of trametinib. Moreover, the experiments conducted herein showed that conditional expression of Braf$^{V600E}$ in mouse keratinocytes results in the development of a range of GVHD relevant skin and oral lesions. Topical MEK-inhibition effectively regressed skin and oral lesions, and prevented animal death. It was also shown that MEK activation is increased in epidermal and dermal cells of human GVHD lesional skin samples. Together, these results indicate that MEK activation is not only crucial for alloreactive T-cell proliferation, but also acts in skin cells to provoke GVHD relevant skin lesions, suggesting that topical MEK-inhibition will prevent or alleviate GVHD.

Lastly, the BRAF/MEK/ERK signaling axis plays a pivotal role in itch or pruritus which is associated with a wide range of skin abnormalities including allergic contact dermatitis, sun-burn, psoriasis and side effects of therapeutics. Induction of Braf mutation in mouse Nav1.8+ neuronal cells results in elevated expressions of itch-sensing genes, including gastrin-releasing peptide and MAS-related GPCR member A3, and consequently, these animals showed markedly enhanced pruriceptor excitability and scratching behavior. In addition, MEK/ERK signaling in keratinocyte is required for TRPV4 ion channel-evoked itch. These data demonstrates that sustained MEK/ERK signaling is required both in sensory neurons and keratinocytes for the initiation and maintenance of a chronic itch sensation. Topical MEK inhibition represents a new modality for itch associated with the wide array of skin disorders.

Accordingly, the instant disclosure is based, at least in part, upon the discovery that topical administration of MEK inhibitors for the treatment of skin disorders (e.g., skin cancer, inflammatory skin disorders) requires markedly reduced dosage levels in comparison with oral administration dosage levels. Such discovery has thereby inspired a new strategy for treatment or prevention of such skin disorders in a subject—specifically, one based upon topical administration of a MEK inhibitor to the subject. Topical application of MEK inhibitors (e.g., trametinib, cobimetinib, binimetinib, selumetinib, and tetrathiomolybdate) for treatment or prevention of skin disorders (e.g., skin cancer, inflammatory skin disorders) and/or an associated disease or disorder is specifically contemplated.

In certain embodiments, the present invention provides methods for treating or preventing skin disorders in a subject through topical administration of a MEK inhibiting agent to a region of the subject's skin experiencing the skin disorder, thereby treating or preventing the skin disorder.

In some embodiments, the topical administration of a pharmaceutical composition to the area in need of treatment results in percutaneous absorption of the MEK inhibiting agent into the skin.

Such methods are not limited to treating a particular type or kind of skin disorder.

In some embodiments, the skin disorder is any type of skin disorder characterized by a Braf mutation.

In some embodiments, the skin disorder is a skin cancer (e.g., squamous cell carcinoma (SCC), basal cell carcinoma (BCC), hyperkeratosis, actinic keratosis, sebaceous adenoma, UV induced skin cancer, and syringoma). Topical treatment of such skin cancers with MEK inhibiting agents is desirable.

In some embodiments, the skin disorder is an inflammatory skin condition (e.g., atopic dermatitis, GVHD, psoriasis, and pruritus). Inflammation of the skin is a symptom of many dermal diseases and conditions. Such inflammatory skin conditions include, for example, atopic dermatitis, bullous disorders, collagenoses, psoriasis, psoriatic lesions, seborrheic dermatitis or contact dermatitis, eczema, urticaria, pruritus, rosacea, prurigo nodularis, hypertrophic scarring, keloid scar formation, scleroderma, Folliculitis keloidalis nuchae, Kawasaki Disease, Sjögren-Larsson Syndrome, Grover's disease, first, second, third and fourth degree burns, cutaneous mucinosis, solar keratosis, GVHD, and pruritus. Topical treatment of such inflammation in these conditions with MEK inhibiting agents is desirable.

In some embodiments, the skin disorder is selected from the group comprising scarring, dermatitis, a proliferative disease or condition, a mast cell disease or condition, a burn or contact with an allergen and/or an irritant.

In some embodiments, the skin disorder is selected from the group comprising atopic dermatitis, bullous disorders, collagenoses, psoriasis, psoriatic lesions, seborrheic dermatitis or contact dermatitis, eczema, urticaria, pruritus, rosacea, prurigo nodularis, hypertrophic scarring, keloid scar formation, scleroderma, Folliculitis keloidalis nuchae, Kawasaki Disease, Sjögren-Larsson Syndrome, Grover's disease, a first degree burn, a second degree burn, a third degree burn, a fourth degree burn, cutaneous mucinosis, solar keratosis, squamous cell carcinoma or melanoma, asteatotic eczema, discoid eczema, hand eczema, gravitational/varicose eczema, eczematous drug eruptions, lichen simplex, lichen sclerosus, lichen planus Irritant, allergic contact dermatitis, photoallergic/photoaggravated dermatitis, infective (secondary to bacterial/viral/fungal infection) dermatitis, pruritic diseases including those associated with chronic systemic disorders such as uremic pruritus, cholestatic pruritus, adult blaschkitis, aquadynia, aquagenic pruritus, balsam of Peru, biliary pruritus, brachioradial pruritus, drug-induced pruritus, hydroxyethyl starch-induced pruritus, itchy points, lichen simplex chronicus, neurodermatitis, prion pruritus, prurigo, prurigo pigmentosa, prurigo simplex, pruritus ani, pruritus scroti, pruritus vulvae, puncta pruritica, referred itch, renal pruritus, scalp pruritus, senile pruritus, xerotic eczema, itch associated with HIV infection, T-cell lymphoma, Sezary syndrome and mycosis fungoides.

Previously researchers have investigated the treatment of skin cancers and inflammatory skin conditions through MEK inhibition via the oral and pulmonary routes. In general, these treatments have focused on optimizing therapeutic agents for the oral route.

In general, the oral route is a suboptimal method to treat diseases of the skin. In particular, systemic administration (via the oral route or otherwise) carries with it the risk of side effects in tissues unconnected with the condition, for example gastrointestinal irritation and/or toxicity. Furthermore, compounds administered orally are subject to first pass metabolism via the liver. Instead, topical administration would frequently be the route of choice, if it could be achieved. The topical administration of a drug has many advantages in the treatment of a localized condition. Since the drug is made available at the site where it is required, an equivalent concentration of the drug circulating systemically is avoided. This can lessen or eliminate the side effects mentioned above.

Indeed, a drawback for oral administration and pulmonary administration of such MEK inhibiting agents is the high drug amounts required to achieve a therapeutic benefit and the associated substantial side effects on the digestive system, discouraging its use for non-malignant diseases. As noted, experiments conducted herein discovered that topical administration of MEK inhibitors for the treatment of skin disorders (e.g., skin cancer, inflammatory skin disorders) requires markedly reduced dosage levels in comparison with oral administration dosage levels thereby avoiding substantial side effects on the digestive system.

Many MEK inhibiting agents suitable for topical administration have been identified including trametinib (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1 (2H)-yl}phenyl)acetamide). Trametinib is a lipophilic compound with proven favorable pharmacokinetic properties. Like many other oncokinase inhibitors, oral trametinib is associated with substantial side effects on the digestive system, discouraging its use for non-malignant diseases. The feasibility of topical administration trametinib has not been established. As noted, in experiments conducted herein, the in vivo effects of topical trametinib were assessed on three different animal skin disease models, including the oncogenic Braf-driven skin cancer and inflammation model, the 2,4-dinitrofluorobenzene (DNFB)-induced atopic dermatitis, and the imiquimod (IMQ)-induced psoriasis model. As noted, it was shown that topical application of trametinib for the treatment of skin disorders (e.g., skin cancer, inflammatory skin disorders) requires markedly reduced dosage levels in comparison with oral application.

Additional MEK inhibiting agents suitable for topical administration include pyrrole derivatives, TAK-733 (one of a series of 8-methylpyrido[2,3-d]pyrimidine-4,7(3H,8H)-dione derivatives), CH4987655 and RDEA119/BAY 869766, cobimetinib ((S)-[3,4-Difluoro-2-(2-fluoro-4-iodophenylamino)phenyl][3-hydroxy-3-(piperidin-2-yl)azetidin-1-yl]methanone), binimetinib(5-((4-bromo-2-fluorophenyl) amino)-4-fluoro-N-(2-hydroxyethoxy)-1-methyl-1H-benzo [d]imidazole-6-carboxamide), selumetinib (6-(4-bromo-2-chloroanilino)-7-fluoro-N-(2-hydroxyelhoxy)-3-methylbenzimidazole-5-carboxamide), tetrathiomolybdate, PD-325901, CI-1040, PD035901 or TAK-933.

Such methods are not limited to a particular dosage for the MEK inhibiting agent or concentration of the MEK inhibiting agent within the composition.

In some embodiments wherein the disorder is a type of skin cancer (e.g., squamous cell carcinoma (SCC), basal cell carcinoma (BCC), hyperkeratosis, actinic keratosis, sebaceous adenoma, UV induced skin cancer, and syringoma), the dosage of the MEK inhibiting agent is approximately 10× less than a therapeutically effective systemic application dosage for the same MEK inhibiting agent. For example, in some embodiments wherein the disorder is a skin cancer and the MEK inhibiting agent is trametinib, the therapeutically effective dose is approximately 0.2 mg (e.g., 10× less than a therapeutically effective oral dosage for trametinib in the treatment of melanoma or the same type of skin cancer) (e.g., 0.01 mg, 0.05 mg, 0.1 mg, 0.13 mg, 0.15 mg, 0.199 mg, 0.2, 0.22, 0.23, 0.25, 0.28, 0.29, 0.3, 0.35, 0.4, 0.5, 0.6, 0.99, etc.).

In some embodiments wherein the disorder is a type of skin cancer (e.g., squamous cell carcinoma (SCC), basal cell carcinoma (BCC), hyperkeratosis, actinic keratosis, sebaceous adenoma, UV induced skin cancer, and syringoma), the concentration of the MEK inhibiting agent within the composition is between approximately 0.03 mM and 2 mM (e.g., between 0.01 mM and 4 mM) (e.g., between 0.0199 mM and 3.5 mM) (e.g., between 0.025 mM and 3 mM) (e.g., between 0.026 mM and 2.5 mM) (e.g., between 0.0299 mM and 2.01 mM).

In some embodiments wherein the disorder is a Braf-induced tumor, the concentration of the MEK inhibiting agent within the composition is approximately 1.5 mM (e.g., 0.85 mM, 0.9 mM, 0.95 mM, 1 mM, 1.2 mM, 1.3 mM, 1.5 mM, 1.51 mM, 1.6 mM, 1.8 mM, 2.2 mM, 2.99 mM).

In some embodiments wherein the composition is used to prevent UV-induced skin cancer, the concentration of the MEK inhibiting agent within the composition is approximately between 10 μM and 30 μM (e.g., 5 μM and 35 μM) (e.g., 7 μM and 32 μM) (e.g., 9.5 μM and 36.5 μM) (e.g., 9.99 μM and 30.001 μM) (e.g., 11 μM and 32 μM) (e.g., 15 μM and 25 μM).

In some embodiments wherein the disorder is an inflammatory skin disorder, the concentration of the MEK inhibiting agent within the composition is approximately between 0.2 mM and 60 mM (e.g., 0.01 mM and 75 mM) (e.g., 0.05 mM and 70 mM) (e.g., 0.099 mM and 65 mM) (e.g., 0.015 mM and 62.5 mM) (e.g., 0.199 mM and 60.001 mM) (e.g., 0.3 mM and 59 mM) (e.g., 0.5 mM and 55 mM) (e.g., 0.75 mM and 50 mM).

In some embodiments wherein the skin disorder is an inflammatory skin condition (e.g., atopic dermatitis, GVHD, psoriasis, and pruritis), the dosage of the MEK inhibiting agent is approximately 10,000× less than a therapeutically effective oral dosage for the same MEK inhibiting agent for treating the same inflammatory skin condition.

Any dosage ranges, concentration ranges, percentage range, or ratio range recited herein are to be understood as expressly disclosing and including any concentrations, percentages or ratios of any integer within that range and fractions thereof, such as one tenth and one hundredth of an integer, and any sub-range falling within a range, unless otherwise indicated.

Such methods are not limited to a type of subject. In some embodiments, the subject is a human subject. In some embodiments, the subject is a mammalian subject.

In certain embodiments, the MEK inhibiting agents are useful in the preparation of a pharmaceutical formulation, also synonymously referred to herein as "medicaments," to treat such skin conditions through topical administration. In addition, such pharmaceutical formulations configured for topical administration are useful for treating additional conditions wherein effectiveness of MEK inhibiting agents are known or predicted (e.g., non-Hodgkins lymphoma, colorectal cancer, malignant melanoma, papillary thyroid carcinoma, non-small-cell lung carcinoma, adenocarcinoma, hairy cell leukemia, lung cancer, brain tumors, including glioblastoma and pilocytic astrocytomas, and the like).

The methods and techniques for preparing pharmaceutical formulations or medicaments of a MEK inhibiting agent for topical application are well-known in the art. Exemplary pharmaceutical formulations and routes of delivery are described below.

Pharmaceutically acceptable salts of the MEK inhibiting agents having an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri lower alkylamine, for example ethyl-tert-butyl-, diethyl-, diisopropyl-, triethyl-, tributyl- or 5 dimethylpropylamine, or a mono-, di-, or trihydroxy lower alkylamine, for example mono-, di- or triethanolamine.

The term "topical administration" relates to the application of a substance directly to a body surface, such as the skin. In particularly preferred embodiments, the topical administration is epicutaneous, i.e., directly onto the surface of the skin. This may sometimes be referred to as dermal administration. The composition may be provided in any form suitable for topical administration, including but not limited to ointments, gels, creams, lotions, oil-in-water (o/w) emulsions, water-in-oil (w/o) emulsions, oil in water in oil (o/w/o) emulsions, water in oil in water (w/o/w) emulsions, microemulsions, foams, sprays, mousses, patches, powders, pastes, medicated plasters and the like, using well known techniques and excipients. In some embodiments, composition is provided in the form of a cream, ointment, lotion or gel. In some embodiments, the composition is provided in the form of a cream or an ointment.

In preferred embodiments, the MEK inhibiting agent or pharmaceutically acceptable salt thereof is present at from about 0.01% to about 10% (w/w). More preferably the MEK inhibiting agent or pharmaceutically acceptable salt thereof is present at from about 0.3% to about 3%. In other preferred embodiments the MEK inhibiting agent or pharmaceutically acceptable salt thereof is present at about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10% (w/w).

In some embodiments, the composition includes a carrier, wherein the carrier may be a solvent in which the active component (e.g., MEK inhibiting agent) is soluble.

Suitable solvents include, but are not limited to water (about 0-about 25% w/w); alcohols (about 0-about 20% w/w) selected from monohydric alcohols having from 1 to 18 carbons, such as methanol, ethanol, propanol, isopropanol, butanol, hexanol, cetyl alcohol, stearyl alcohol, and the like; dihydric and polyhydric alcohols, such as propylene glycol, glycerol; hexanetriols, such as 1,2,6-hexanetriol, sorbitol, 1,3-butanediol, 2,3-butanediol, etc.; lower alkyl ethers of glycols having from 1 to 6 carbons such as the monomethyl or monoethyl ether of ethylene or diethylene or propylene or dipropylene glycol, propylene glycol or dipropylene glycol monomethyl ethers, diethylene glycol monoethyl ether, ethylene glycol monomethyl ether, etc; polyethylene glycols having molecular weights of from 100 to 8,000, preferably in the range 4,000; esters of aliphatic monobasic and dibasic acids having from 2 to 22 carbons and monohydric alcohols having from 1 to 20 carbons, di- and polyhydric alcohols having from 2 to 20 carbons, and sugar alcohols such as isopropyl myristate, isopropyl palmitate, myristyl myristate, cetyl stearate, methyl stearate, isopropyl sebacate, methyl sebacate, sucrose monolaurate, sucrose monostearate, and the like. Other suitable solvents include mannitol, xylitol, sorbitol and monohydric alcohols having from 1 to 6 carbons in the range of 0-20% (w/w), such as methanol, ethanol, propanol, isopropanol, butanol, or hexanol.

In some embodiments, the solvent may comprise a non-toxic glycol or glycol ether selected from the group consisting of propylene glycol, butylene glycol, diethylene glycol and diethylene glycol ether. Other solvents include, but are not limited to, ethanol, deionised water, benzyl alcohol, PEG 400, dimethyl isosorbide (Arlasolve dmi), diethylene glycol monoethyl ether (Transcutol P), glycerin (glycerol), isopropyl myristate (IPM), isopropanol (isopropyl alcohol), octyldodecanol, phenoxyethanol, oleyl alcohol, mineral oil (liquid paraffin), Crodamol GTCC (caprylic/capric triglyceride or medium chain triglycerides), castor oil, isopropyl palmitate (IPP), propylene glycol dicaprylate/dicaprate and apricot kernel oil PEG-6 esters (Labrafil M1944CS).

The composition may also include a co-solvent, which may be selected from the list of solvents provided above. In particular, the co-solvent is selected from the group comprising of water, mannitol, xylitol, sorbitol and monohydric alcohols having from 1 to 6 carbons in the range of 0-20% (w/w), such as methanol, ethanol, propanol, isopropanol, butanol, or hexanol; and when another co-solvent is selected from one or more of the group consisting of propylene glycol (in the range 0-35% w/w), glycerol (in the range 0-10% w/w), polyethylene glycols such as PEG400 (in the range 0-80% w/w) or PEG4000 (or similar molecular weight agents in the class) (in the range 0-30% w/w).

Furthermore, two or more different solvents may be combined into solvent systems with desirable properties.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Where composition is in the form of an emulsion (oil-in-water (o/w), water-in-oil (w/o) oil in water in oil (o/w/o) and water in oil in water (w/o/w)), the composition may further comprise an emulsifier. This may be included to adjust the size of the droplets of oil in the oil phase, which may have a diameter of up to 200 µm, to a smaller size, typically in the range of 1-50 µm, thereby improving the cosmetic appearance of the composition. The emulsifier may suitably be a water-in-oil emulsifier, e. g. selected from the group consisting of water-in-oil emulsifiers such as, for example, polyoxyalkylene C12-20 alkyl ethers, such as polyoxyethylene-2-cetyl ether, polyoxyethylene-2-lauryl ether, polyoxyethylene-2-oleyl ether or polyoxyethylene-2-stearyl ether, polyoxyalkylene alkyl esters, sorbitan oleate, sorbitan isostearate, sorbitan sesquioleate, glycerol esters of isostearic acid and adipic acid, polyglyceryl-3-diisostearate and polyglyceryl-6-hexaricinoleate. The emulsifier may suitably be a oil-in-water emulsifier, e.g. selected from the group consisting of oil-in-water emulsifiers such as, for example, polyoxyalkylene C12-20 alkyl ethers and esters, such as polyoxyethylene-20-cetyl ether, polyoxyethylene-20-lauryl ether, polyoxyethylene-20-oleyl ether or polyoxyethylene-20-stearyl ether, polysorbate 20, polysorbate 60, polysorbate 80 and the like.

The composition of the present invention may be prepared in accordance with methods well known to the person skilled in the art of pharmaceutical formulation. The amount of the individual ingredients in the composition will, to some extent, depend on the concentration of the active component incorporated therein. The amount of active component in the composition may vary widely according to the severity of the condition to be treated, the age and condition of the patient and the discretion of the physician.

In addition to the above-mentioned ingredients, the present composition may include one or more additional ingredients such as other therapeutically active substances applied in the treatment of skin disorders (e.g., skin cancer, inflammatory skin disorders), including antineoplastic agents (e.g., fluorouracil, interferon alpha-2b, vismodegib, sonidegib), photosensitizing agents (e.g., methyl aminolevulinate), keratolytic agents (e.g., tazarotene), and imiquimod.

In addition to the above-mentioned ingredients, the present composition may include one or more additional ingredients such as other therapeutically active substances applied in the treatment of skin disorders (e.g., skin cancer, inflammatory skin disorders), including corticosteroids such as hydrocortisone; non-steroidal anti-inflammatories such as salicylic acid, salicylates, Vitamin D analogues such as calcipotriol (Dovonex), immunophilins, p38 kinase inhibitors, calcineurin inhibitors such as Tacrolimus and Pimecrolimus; and cannabinoids; vasomodulators such as alpha adrenoreceptor ligands; and topical anesthetics such as bupivacaine, chlorprocaine, dibucaine, ketamine and pramoxine; anti-infectives such as topical antibiotics such as clindamycin; antifungals; antivirals; Histamine $H_1$ receptor antagonists; Histamine $H_2$ receptor antagonists; Histamine $H_3$ receptor antagonists; Leukotriene antagonists, including antagonists of $LTB_4$, $LTC_4$, $LTD_4$, and $LTE_4$, for example Montelukast; Phosphodiesterase inhibitors, including PDE3 inhibitors, PDE4 inhibitors, PDE5 inhibitors, PDE7 inhibitors and inhibitors of two or more phosphodiesterases, such as dual PDE3/PDE4 inhibitors; neurotransmitter re-uptake inhibitors, in particular fluoxetine, sertraline, paroxetine, ziprasidone; 5-Lipoxygenase (5-LO) inhibitors or 5-lipoxygenase activating protein (FLAP) inhibitors; $\alpha_1$- and $\alpha_2$-adrenoceptor agonist vasoconstrictor sympathomimetic agents; Muscarinic $M_3$ receptor antagonists or anticholinergic agents; $\beta_2$-adrenoceptor agonists; Dual acting $\beta_2/M_3$ agents; Xanthines, such as theophylline and aminophylline; Non-steroidal anti-inflammatories, such as sodium cromoglycate and nedocromil sodium; Ketotifen; COX-1 inhibitors (NSAIDs) and COX-2 selective inhibitors; Oral, inhaled, intranasal and topical glucocorticosteroids; Monoclonal antibodies active against endogenous inflammatory entities; Anti-tumor necrosis factor (anti-TNF-α) agents; Adhesion molecule inhibitors including VLA-4 antagonists; Kinin-$B_1$- and $B_2$-receptor antagonists; Immunosuppressive agents; Inhibitors of matrix metalloproteases (MMPs); Tachykinin $NK_1$, $NK_2$ and $NK_3$ receptor antagonists; Elastase inhibitors; Adenosine A2a receptor agonists; Inhibitors of urokinase; Compounds that act on dopamine receptors, e. g. D2 agonists; Modulators of the NFKb pathway, e. g. IKK inhibitors; Agents that can be classed as mucolytics or anti-tussive agents; Antibiotics; Modulators of cytokine signaling pathways, such as p38 MAP kinase inhibitors, SYK kinase inhibitors or JAK kinase inhibitors; Modulators of the prostaglandin pathways, including inhibitors of H-PDGS and antagonists of DP-1 and CRTH2; Antagonists of chemokine receptors CXCR1 and CXCR2; Antagonists of chemokine receptors CCR3, CCR4 and CCR5; Inhibitors of phosphoinositide-3-kinase; HDAC inhibitors; p38 inhibitors; CXCR2 antagonists; Calcineurin inhibitors; Anti-interleukin 17 (anti-IL-17) agents; Anti-interleukin 4 receptor (anti-IL4R) agents; or Anti-interleukin 31 (anti-IL-31) agents.

The effect the active agent or agents in any formulation may be enhanced by use of agents to enhance dermal penetration. Examples of suitable agents to enhance dermal penetration are disclosed at Int J Pharm. 2013 Apr. 15; 447(1-2):12-21. Thus, the composition of the present invention may include one or more penetration enhancers. Penetration enhancers include but are not limited to dimethyl sulfoxide (DMSO), 2-(2-Ethoxyethoxy)ethanol and dimethyl isosorbide in the range of 5-30% (w/w). Other non-limiting examples of penetration enhancers include C8-C22 fatty acids such as isostearic acid, octanoic acid, and oleic acid; C8-C22 fatty alcohols such as oleyl alcohol and lauryl alcohol; lower alkyl esters of C8-C22 fatty acids such as ethyl oleate, isopropyl myristate, butyl stearate, and methyl laurate; di(lower)alkyl esters of C6-C8 diacids such as diisopropyl adipate; monoglycerides of C8-C22 fatty acids such as glyceryl monolaurate; tetrahydrofurfuryl alcohol polyethylene glycol ether; polyethylene glycol; propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; terpenes; macrocyclic enhancers such as macrocyclic ketones, for example, 3-methylcyclopentadecanone, 9-cycloheptadecen-1-one, cyclohexadecanone, and cyclopentadecanone; macrocyclic esters such as pentadecalactone.

The composition of the invention may include water, but it may also be substantially or totally free of water. Preferably, the water content of the composition is from about 0 to about 80% (w/w).

The present composition may also comprise other components commonly used in topical formulations, including but not limited to antioxidants (e.g. alpha-tocopherol, butylated hydroxytoluene, butylated hydroxyanisole), stabilizers, chelating agents, thickeners, softeners, lubricants, preservatives, emollients, pigments, fragrances, skin soothing agents, skin healing agents and skin conditioning agents such as urea, glycerol, allantoin or bisabolol.

The composition may also comprise a surfactant or emulsifier including, but not limited to, apricot kernel oil PEG-6 esters (Labrafil M1944CS), ceteareth-12 (Brij C20), caprylocaproyl macrogol-8 glycerides (Labrasol), cetostearyl alcohol, glycerol monostearate, lauroyl macrogol-6 glycerides (Labrafil M2130CS), macrogol 15 hydroxystearate, (polyoxyl 15 hydroxystearate), macrogol cetostearyl ether (cetomacrogol 1000), PEG-100 stearate (Myrj S100), polyoxyl 35 castor oil (macrogolglycerol ricinoleate), polyoxyl 40 hydrogenated castor oil, PEG-40 stearate (macrogol stearate, polyoxyl stearate), polysorbate 60 (Tween 60), polysorbate 80 (Tween 80), Span 60 (sorbitan monostearate), steareth-2(Brij S2), steareth-20 (Brij S20), and stearic acid.

The composition may also include one or more viscosity-increasing agents. Viscosity-increasing agents include, but are not limited to polyvinylpyrrolidone, polyvinylpolypyrrolidone (crospovidone), methyl cellulose, hydroxypropyl cellulose (HPC), hydroxypropyl methylcellulose (hypromellose, HPMC), hydroxyethyl cellulose (HEC), xanthan gum, Carbopol (carbomer), and sodium hyaluronate (hyaluronic acid).

Some embodiments of the present invention provide methods for administering an effective amount of a topical composition comprising a MEK inhibiting agent and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

The invention also provides kits comprising a topical composition comprising a MEK inhibiting agent and instructions for administering the compound to an animal. The kits may optionally contain other therapeutic agents (e.g., anticancer agents or apoptosis-modulating agents) (e.g., therapeutic agents useful in treating any type of cancer) (e.g., therapeutic agents useful in treating any type of skin disorder).

Experimental

The following examples are provided to demonstrate and further illustrate certain preferred embodiments of the present invention and are not to be construed as limiting the scope thereof.

EXAMPLE I

This example demonstrates that a keratinocyte targeted oncogenic Braf mutation results in postnatal lethality with inflammatory skin defects.

Figure 1:
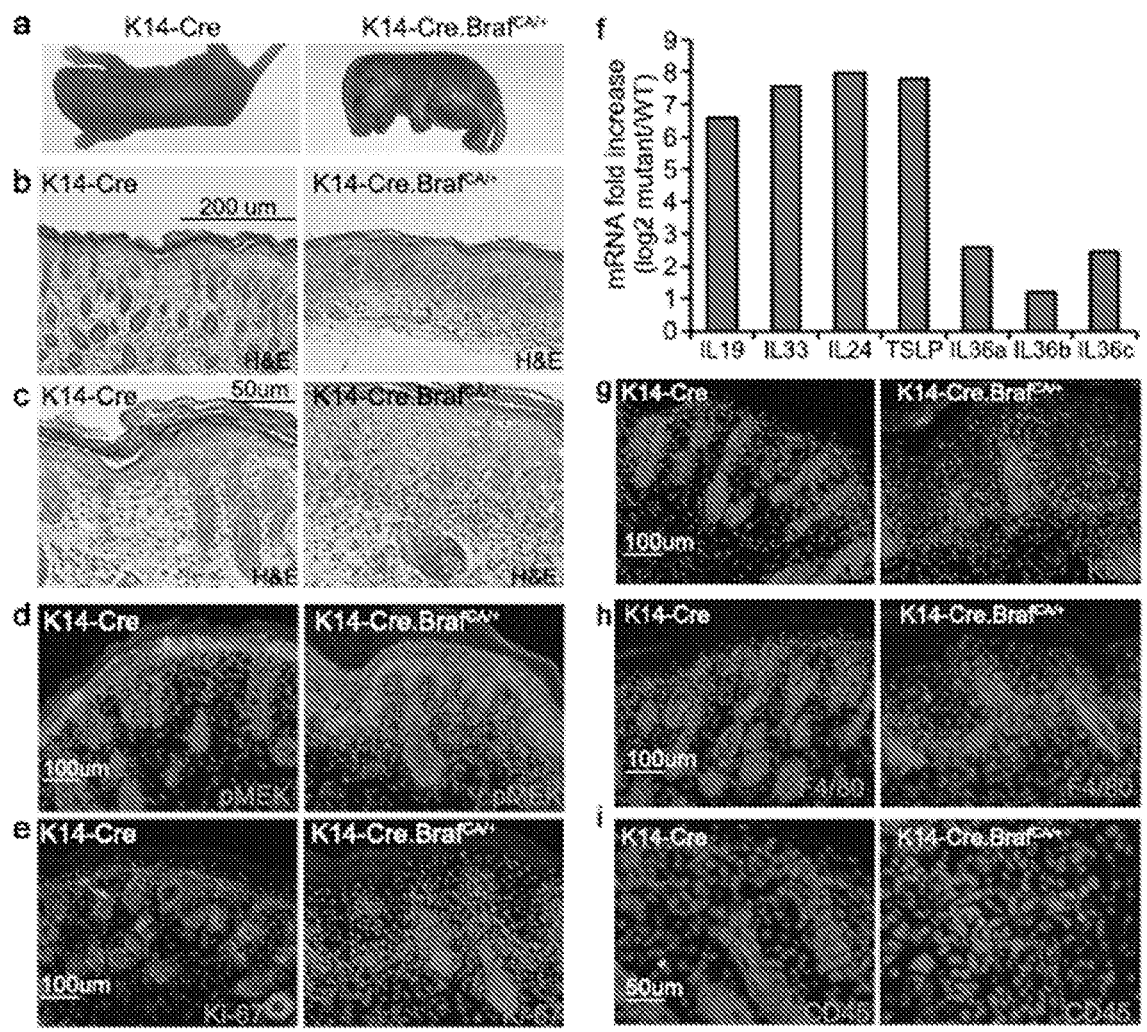
FIG. 1: Epidermis-targeted embryonic Braf mutation results in postnatal lethality with epidermal and hair follicle defects and skin inflammation. (a) Images of K14-Cre and K14-Cre.BrafCa/+ newborn mice. These pups die within 24 hours after birth. (b-c) H&E staining of newborn mouse skin. (d-e) Immunostaining of skin sections with primary antibodies against pMEK and Ki-67 followed by detection with an Alexa-555 [gray-scaled orange] and counterstaining with Hoechst 33825 [gray-scaled blue]. (f) Relative mRNA log-fold changes of inflammatory cytokines in Braf mutant verses WT mice skins (RNA-Seq data, NCBI Accession #SUB373241). (g-i) Immunostaining of skin sections with primary antibodies against K6, F4/80 [gray-scaled green], and CD45 [gray-scaled orange] followed by detection with an Alexa-555 [gray-scaled orange] or Alexa-488 [gray-scaled green] conjugated antibody and counterstaining with Hoechst 33825.

To examine the impact of MEK activation in keratinocytes, Braf-floxed (Braf$^{Ca/+}$) mice were crossed with the K14-Cre transgenic mice. The resulting K14-Cre.Braf$^{Ca/+}$ compound animals express a constitutively active Braf$^{V600E}$ mutant in keratinocytes starting around embryonic day 14. These pups died shortly after birth with severe dermatological defects (see, FIG. 1a). Histological analysis revealed that the mutant newborn skin lacked hair follicles and contained a thickened epidermis and a highly vascularized dermis (see, FIG. 1b-c). As expected, phosphorylated MEK was expressed at a markedly increased level in the mutant epidermis compared to WT skin (see, FIG. 1d). Cell proliferation was detected in both basal and superbasal layers of the mutant epidermis (see, FIG. 1e). Analysis of the RNA-seq data showed that the mutant epidermis expressed significantly increased levels of inflammatory molecules including a range of cytokines, such as IL19, IL33, IL24, TSLP, and IL36 (see, FIG. 10. Consistently, the mutant skins were highly inflamed, as demonstrated by the increased expressions of cytokeratin 6 (CK6) and CD45+ and F4/80 immune cells (see, FIGS. 1g-i). These data indicate that uncontrolled MEK activation in keratinocytes results in developmental skin defects, and induces skin inflammation.

EXAMPLE II

This example demonstrates that epidermis-targeted Braf mutation in adults induces epidermal and sweat gland neoplasia.

In order to understand the effect of Braf-mutation on adult skin, K5-CreER.Braf$^{Ca/+}$ mice were generated, and Braf mutation induced by two consecutive daily doses of 4-hydroxytamoxifen (4-OHT) on the back skin, the ear and the footpads of 2-3 months old mice. By 10$^{th}$ day after 4-OHT, the treated areas showed apparent thickening (see, FIG. 2a). Histological analysis showed that the 4-OHT treated back and the ear skins developed epidermal neoplasia (see, FIGS. 2b-c), and the dermis of the 4-OHT treated footpads contained markedly increased sweat gland nodules with abundant vascularization (see, FIG. 2d). These data indicate that activating Braf mutation in epidermal cells induces epidermal and sweat gland neoplasia.

EXAMPLE III

This example demonstrates that topical trametinib effectively treats skin and oral lesions of Braf mutant mice.

Experiments were conducted that tested whether topical dose trametinib can effectively treat the skin lesions induced by Braf mutation. To do this, Braf mutation was induced in the rear back skins of 2-month old K5-CreER.Braf$^{Ca/+}$ mice with 4-OHT, and 7 days later, applied five consecutive daily topical doses of trametinib (see, FIG. 3a). At day 7 after 4-OHT induction, the treated areas developed skin tumors which were completely regressed by topical trametinib by day 11, as indicated by the clinical images (see, FIG. 3b). Histological analysis showed that topical trametinib not only regressed epidermal neoplasia (see, FIG. 3c), but also reduced CD8+ immune cells in the dermis (see, FIG. 3d). In addition, topical delivery appeared to be more effective than systemic delivery of the same amount to trametinib in treating oral lesions (see, FIG. 3e). These results indicate that topical trametinib effectively regresses mutant Braf induced epidermal neoplasia and inflammation.

EXAMPLE IV

This example demonstrates that topical trametinib effectively treats DNFB-induced skin inflammation.

DNFB is an industrial compound that causes contact dermatitis in human. When applied to Nc/Nga and C57/BL6 mice, DNFB induces dermatitis through CD8+ T-cells. The DNFB-induced skin inflammation has been widely used as an in vivo AD model due to its resemblance to human AD. IMQ is a TLR7/8 ligand and a potent immune activator. Topical cream containing 5% IMQ is commonly used to treat superficial basal cell carcinomas and genital and perianal warts. Serendipitously, this treatment exacerbates psoriasis in patients whose psoriasis has been previously well-controlled. In agreement with the clinical observation, topical applications of IMQ on C57/BL6 and Nc/Nga mice induces itchy inflammatory skin lesions through IL-23/IL-17 signaling axis and CD8+ T-cells, closely replicating human plaque psoriasis. The IMQ-induced psoriasis model has been widely used for in vivo therapeutic screening.

To further assess whether topical trametinib has implications for other inflammatory skin conditions, its effect on the DNFB-induced atopic dermatitis model was tested. To do this, the left and right ear lobes of 3-4 months old C57/BL6 mice were treated with one dose solvent (acetone:olive oil mixed at 4:1 vol/vol) and 0.3% DNFB, respectively. Both ears were then treated daily topical dose trametinib at concentrations ranging from 0, 0.2, 2 to 20 µM. For acute response, ear thickness was measured using a digital caliber at 0, 3, 6, 24, and 48 hours following DNFB treatment. For delayed response, the right ear lobes were re-challenged with one dose of 0.5% DNFB followed by daily dose trametinib for 7 consecutive days and the ear thickness was measured daily. It was found that the thickness of the control ears was not significantly affected by topical trametinib, as indicated by the time-course responses of the left ear lobes (see, FIG. 4a). DNFB induced a mild increase of ear swelling during the acute phase and a second DNFB challenge increased ear swelling by over 10-fold (see, FIG. 4b). The DNFB-induced ear swelling was reduced by trametinib at a dose response manner (see, FIG. 4b). Clinically, the DNFB challenged right ear lobes of the solvent and 0.2 µM trametinib groups appeared thickened and inflamed, whereas those treated with 20 µM trametinib appeared smooth and normal (see, FIG. 4c). Histological analysis showed that DNFB-treated skins contained a markedly thickened epidermis and a dermis with increased cellular infiltration, which were normalized by topical trametinib (see, FIG. 4d). These findings indicate that topical trametinib is effective in inhibiting DNFB-induced dermatitis.

EXAMPLE V

This example demonstrates that topical trametinib mitigates UV-induced skin carcinogenesis.

UV is a primary cause of melanoma and non-melanoma skin cancer. To assess whether topical trametinib inhibits UV-induced skin carcinogenesis, SKH animals (n=10, 5 male and 5 female) were irradiated biweekly with 160 mJ broad band UVB along with pretreatment of solvent or trametinib. The results indicated that animals treated 10 or 30 µM trametinib developed significantly lower number of tumor nodules (FIG. 5).

EXAMPLE VI

This example demonstrates that MEK is activated in human psoriasis and GVHD skin and oral lesions.

To verify the relevance of MEK activation to human psoriasis, immunofluorescent staining for pMEK of a panel of formalin-fixed-paraffin-embedded (FFPE) sections of human psoriatic lesions was performed. It was found that pMEK was highly expressed in the epidermal cells of the lesional skins, and was especially increased in the nuclei of the lesional skin cells compared with normal skin (see, FIG. 5a). Similarly, pMEK was highly expressed in the inflammatory skin and oral lesions of cutaneous graft-vs-host (GVHD) disease of bone marrow transplant patients (see, FIG. 5b). These results indicate that MEK activation is relevant to human psoriatic and GVHD skin and oral lesions.

EXAMPLE VII

Experiments will be conducted to determine the effect of topical trametinib on imiquimod-induced psoriatic lesions.

The effects of topical trametinib on IMQ-induced psoriasis will be assessed. For this, the back skins of 3-4 months old C57/BL6 mice were shaved, and treated with topical applications of 5% IMQ cream along with control solvent and 60 µM trametinib. The skin lesions were assessed clinically using the psoriasis activity and severity index (PASO scale, which ranks severity of erythema (redness), induration (thickness) and desquamation (scale). As expected, 5% IMQ caused erythema, scaling and skin thickening. 60 µM Trametinib reduced the PASI score at day 3, but the differences were minimized by day 5. It was noticed that the severity of the control group did not progress from day 3 to day 5. This dose did not induce animal weight loss and gross morphological changes of internal organs, including liver, kidney and spleen and lymph nodes. However, the results are inclusive, and additional experiments will be conducted to determine the effects of additional dosages including 20 µM which worked for the DNFB-model and different solvent formulations.

Additional experiments will be conducted to investigate the effect of topical trametinib on animal models of cutaneous GVHD. Oral dose trametinib has been previously shown to reduce animal model GVHD. It is anticipated that topical dose trametinib will avoid the detrimental side effects associated with systemic dosing and thus achieve a better clinical outcome for cutaneous GVHD.

EXAMPLE VIII

This example describes the materials and methods for Examples I-VII.

Animal studies were performed in accordance to protocols approved by Duke Animal Care and Use Committee.

Braf mutant animals: K14-Cre and K5-CreER mice were provided by Duke University. These animals were crossed with Tyr-CreER.Braf$^{Ca+/-}$.PTEN−/− mice which were provided by Duke University. Genotyping were performed via PCR. For topical induction, the back skins of adult animals were shaved and treated with two consecutive daily doses of 4-OHT (Sigma, 5 mg/ml in ethanol).

Atopic dermatitis induction with topical 1-Fluoro-2,4-dinitrobenzene (DNFB):12-16 week old C57/BL6 mice were obtained from Duke Animal facility, and randomly divided into 3-5 mice per group. On day 1, the left and right ear lobes (both the internal and the external pinnae) were treated with 5 µl solvent and 0.3% DNFB, respectively. About 5 minutes later, both the left and the right ears were treated with 5 µl trametinib diluted in solvent (acetone:olive oil mixed at 4:1 vol/vol) at concentrations ranging from 0, 0.2, 2 to 20 µM. For acute response, ear thickness was measured using a digital caliber at 0, 3, 6, and 24 hours following DNFB treatment. For delayed response, animals were re-challenged with one dose of 0.5% DNFB and then treated with daily dose trametinib for 7 consecutive days and the ear thickness was measured daily. At the end-point, animals were euthanized for necropsy. Skin, spleen, kidney, lymphoid organs, and liver tissues were examined for gross morphological changes, and then frozen for histological and protein analyses.

UV induction of skin carcinogenesis: Six weeks old hairless SKH-1Elite mice were obtained from (Jackson Laboratory). Animals were subject to UVB irradiation (160-180 mJ dose) 3 times per week for 20 weeks using rayminder model 2 UVB midband lamp M2D24H and UV513AB digital UVA/UVB (280-400 nm) meter of General Tools. Mouse back skins were pretreated before each UV-radiation with 100 µl of solvent (5% DMSO in 95% acetone:olive oil (3:1 mixture) or 10 to 30 µM trametinib (n=5/group/sex).

Psoriasis induction with topical Imiquimod: For imiquimod induction, the front half of mouse back skins were shaved and the remaining hair shafts were removed with Nair hair removal cream. Next day, the shaved areas were treated with topical doses of 62.5 mg (5% Imiquimoid) along with 50 µl solvent (acetone:olive oil 4:1 vol/vol) or 60 µM trametinib and the treatments were repeated daily for 5 consecutive days. The severity of erythema (redness), induration (thickness), and desquamation (scale) were assessed on day 4, 5 and 6 At the end-point, animals were euthanized for necropsy and the skin, spleen, kidney, lymphoid organs, and liver tissues were collected, and frozen for histological and protein analyses.

Histological Analysis

Human tissue sections: Human skin tissues were obtained and used in accordance to an approved IRB protocol. Formalin-fixed-paraffin-embedded (FFPE) tissue sections of human psoriatic lesions and human GVHD skin and oral lesions were obtained from Tianjin Medical School of China and Duke Pathology Lab, respectively. Surgically discarded normal human skin tissues were obtained from Duke Hospital. After standard dewaxing and rehydration, tissue sections were antigen-unmasked via boiling in 10 mM citrate buffer for 10 minutes, immunostained with a primary antibody against phospho-MEK1/2 (Ser217/221) (Cell Signaling Technology), and then detected with a Dylight 549-conjugated anti-rabbit secondary antibody [Jackson Immuno-Research lab] followed by counterstaining with counterstaining with Hoechst 33342 (Sigma-Aldrich).

Mouse tissues: For H&E staining of mouse skins, 5 µm frozen tissue sections were fixed with ethanol and stained with Hematoxylin and Eosin. For immunostaining, 5 µm frozen tissue sections were fixed with cold methanol, incubated with and a primary antibody against CD8 (Tonbo Biosciences), and detected with a secondary antibody conjugated to Dylight 488 (Invitrogen) followed by counterstaining with Hoechst 33342. The images were obtained with the Olympus imaging system.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating a skin disorder in a patient in need thereof, the method comprising topical administration of a pharmaceutical composition to the area in need of treatment, wherein the pharmaceutical composition comprises a therapeutically effective amount of a MEK inhibiting agent and a pharmaceutically acceptable diluent or carrier, wherein the MEK inhibiting agent is present at or between 0.01% and 4% (w/w), wherein the pharmaceutical composition is in a form selected from ointments, gels, creams, lotions, oil-in-water emulsions, water-in-oil emulsions, microemulsions, foams, sprays, mousses, patches, powders, pastes, and medicated plasters, wherein the topical administration of the pharmaceutical composition to the area in need of treatment results in percutaneous absorption of the therapeutically effective amount of the MEK inhibiting agent into the area in need of treatment.

2. The method of claim 1, wherein the MEK inhibiting agent is present at or between 0.01% and 1% (w/w).

3. The method of claim 1, wherein the MEK inhibiting agent is present at or between 0.01% and 0.1% (w/w).

4. The method of claim 1, wherein the pharmaceutical composition also comprises additional therapeutic agents for treating the skin disorder.

5. The method of claim 1, wherein the pharmaceutically acceptable diluent or carrier comprises at least one substance selected from the group comprising water, cetyl alcohol, stearyl alcohol, propylene glycol, glycerol, 1,2,6-hexanetriol, sorbitol, 1,3-butanediol, 2,3-butanediol, monomethyl or monoethyl ether of ethylene or diethylene or propylene or dipropylene glycol, propylene glycol or dipropylene glycol monomethyl ethers, diethylene glycol monoethyl ether, ethylene glycol monomethyl ether, polyethylene glycols isopropyl myristate, isopropyl palmitate, myristyl myristate, cetyl stearate, methyl stearate, isopropyl sebacate, methyl sebacate, sucrose monolaurate, sucrose monostearate, mannitol, xylitol, sorbitol, methanol, ethanol, propanol, isopropanol, butanol, and hexanol.

6. The method of claim 1, wherein the pharmaceutical composition further comprises one or more of the following: an emulsifier, a viscosity-increasing agent, and a penetration enhancer, wherein the penetration enhancer is selected from the group comprising 2-(2-Ethoxyethoxy)ethanol, dimethyl isosorbide, isostearic acid, octanoic acid, oleic acid, oleyl alcohol and lauryl alcohol, ethyl oleate, isopropyl myristate, butyl stearate, methyl laurate, diisopropyl adipate, glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, alkylaryl ethers of polyethylene oxide, polyethylene oxide monomethyl ethers, polyethylene oxide dimethyl ethers, dimethyl sulfoxide, glycerol, ethyl acetate, acetoacetic ester, N-alkylpyrrolidone, terpenes, 3-methylcyclopentadecanone, 9-cycloheptadecen-1-one, cyclohexadecanone, cyclopentadecanone, and pentadecalactone.

7. The method of claim 1, wherein the skin disorder is any skin disorder characterized by a Braf mutation.

8. The method of claim 1, wherein the skin disorder is a skin cancer and/or an inflammatory skin condition.

9. The method of claim 8, wherein the skin cancer is selected from squamous cell carcinoma (SCC), basal cell carcinoma (BCC), hyperkeratosis, actinic keratosis, sebaceous adenoma, UV induced skin cancer, and syringoma.

10. The method of claim 1, wherein the skin disorder is selected from atopic dermatitis, graft-versus host disease (GVHD), psoriasis, and pruritis.

11. The method of claim 1, wherein the MEK inhibiting agent is selected from trametinib (N-(3-{3-Cyclopropyl-5-[(2-fluoro-4-iodophenyl)amino]-6,8-dim ethyl-2,4,7-trioxo- 3,4,6,7-tetrahydropyrido [4,3-d] pyrimidin-1 (2H)-yl} phenyl)acetamide), TAK-733, CH4987655, RDEA119/BAY 869766, cobimetinib ((S)-[3,4-Difluoro-2-(2-fluoro-4-iodophenylamino)phenyl] [3-hydroxy-3-(piperidin-2-yl)azetidin-1-yl] methanone), binimetinib (5-((4-bromo-2-fluorophenyl)amino)-4-fluoro-N-(2-hydroxyethoxy)-1-methyl-1H-benzo[d]imidazole-6-carboxamide), selumetinib (6-(4-bromo-2-chloroanilino)-7-fluoro-N-(2-hydroxyelhoxy)-3-methylbenzimidazole-5-carboxamide), PD-325901, CI-1040, PD035901, tetrathiomolybtate, and TAK-933.

12. The method of claim 1, wherein skin disorder is a skin cancer, wherein the MEK inhibiting agent is trametinib, wherein the dosage amount of the trametinib is approximately 0.2 mg.

13. The method of claim 1, wherein skin disorder is a skin cancer, wherein the dosage of the MEK inhibiting agent is approximately 10× less than a therapeutically effective oral dosage for trametinib in the treatment of melanoma or the same type of skin cancer.

14. The method of claim 1, wherein the disorder is a Braf-induced tumor, wherein the concentration of the MEK inhibiting agent within the composition is approximately 1.5 mM.

15. The method of claim 1, wherein the composition is used to prevent UV-induced skin cancer, wherein the concentration of the MEK inhibiting agent within the composition is approximately between 10 μM and 30 μM.

16. The method of claim 1, wherein the disorder is an inflammatory skin disorder, wherein the concentration of the MEK inhibiting agent within the composition is approximately between 0.2 mM and 60 mM.

17. The method of claim 1, wherein the skin disorder is an inflammatory skin condition, wherein the dosage of the MEK inhibiting agent is approximately 10,000× less than a therapeutically effective oral dosage for the same MEK inhibiting agent for treating the same inflammatory skin condition.

18. A kit comprising a pharmaceutical composition as recited in claim 1 and instructions for topically administering the pharmaceutical composition to a patient having a skin disorder.

* * * * *